(12) United States Patent
Greenhalgh et al.

(10) Patent No.: US 7,581,328 B2
(45) Date of Patent: Sep. 1, 2009

(54) ANATOMICAL MEASUREMENT TOOL

(75) Inventors: E. Skott Greenhalgh, Wyndmoor, PA (US); Stephen J. Kleshinski, San Jose, CA (US)

(73) Assignee: Stout Medical Group, L.P., Perkasie, PA (US)

( * ) Notice: Subject to any disclaimer, the term of this patent is extended or adjusted under 35 U.S.C. 154(b) by 0 days.

(21) Appl. No.: 12/016,965

(22) Filed: Jan. 18, 2008

(65) Prior Publication Data

US 2008/0183105 A1 Jul. 31, 2008

Related U.S. Application Data

(63) Continuation of application No. PCT/US2006/028239, filed on Jul. 19, 2006.

(60) Provisional application No. 60/700,359, filed on Jul. 19, 2005.

(51) Int. Cl.
*A61B 1/00* (2006.01)

(52) U.S. Cl. .......................... 33/512; 33/511; 604/103

(58) Field of Classification Search ........... 33/511–512; 604/103; 623/1.11, 1.12
See application file for complete search history.

(56) References Cited

U.S. PATENT DOCUMENTS

| | | | | |
|---|---|---|---|---|
| 4,787,899 A | * | 11/1988 | Lazarus | 623/1.11 |
| 4,921,484 A | * | 5/1990 | Hillstead | 604/104 |
| 6,273,895 B1 | * | 8/2001 | Pinchuk et al. | 606/108 |
| 6,482,222 B1 | * | 11/2002 | Bruckheimer et al. | 606/200 |
| 7,122,043 B2 | * | 10/2006 | Greenhalgh et al. | 606/191 |
| 2006/0009799 A1 | * | 1/2006 | Kleshinski et al. | 606/200 |
| 2006/0178694 A1 | * | 8/2006 | Greenhalgh et al. | 606/198 |

* cited by examiner

*Primary Examiner*—G. Bradley Bennett
*Assistant Examiner*—Tania C Courson
(74) *Attorney, Agent, or Firm*—Levine Bagade Han LLP

(57) ABSTRACT

A measuring device for measuring tunnel defects in tissue is disclosed. The measuring device can size the defect to aid future deployment of a tissue distension device. Exemplary tunnel defects are atrial septal defects, patent foramen ovales, left atrial appendages, mitral valve prolapse, and aortic valve defects. Methods for using the same are disclosed.

23 Claims, 17 Drawing Sheets

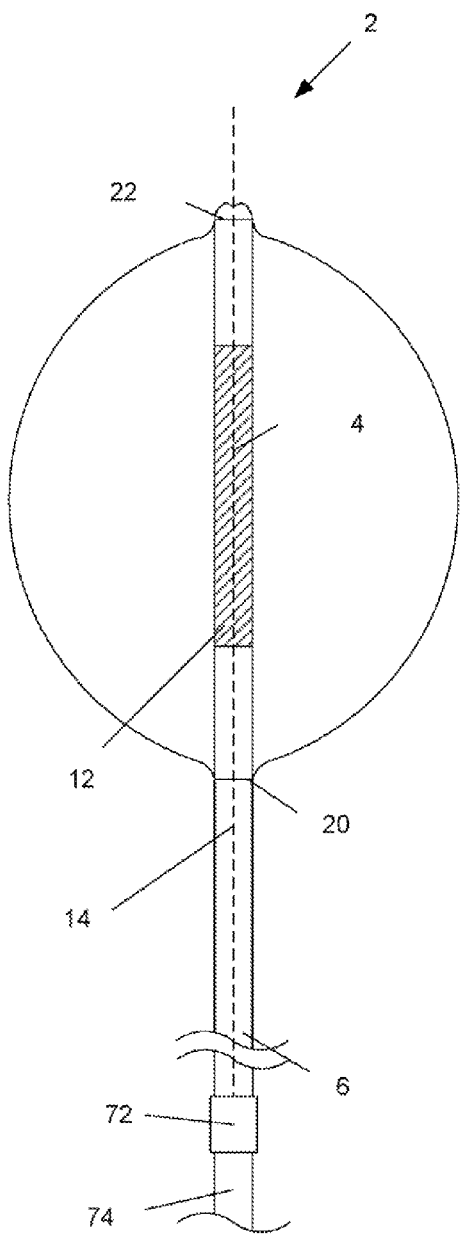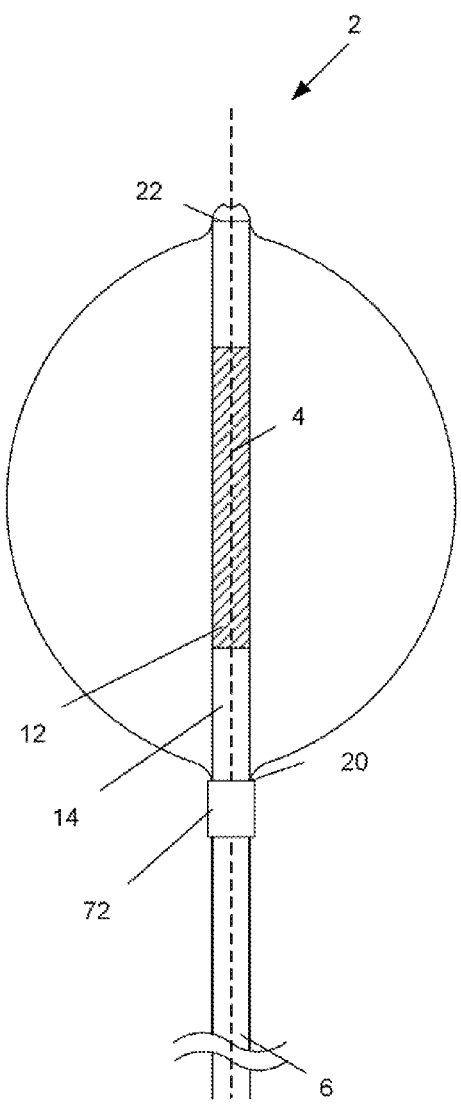
Fig. 22
Fig. 23

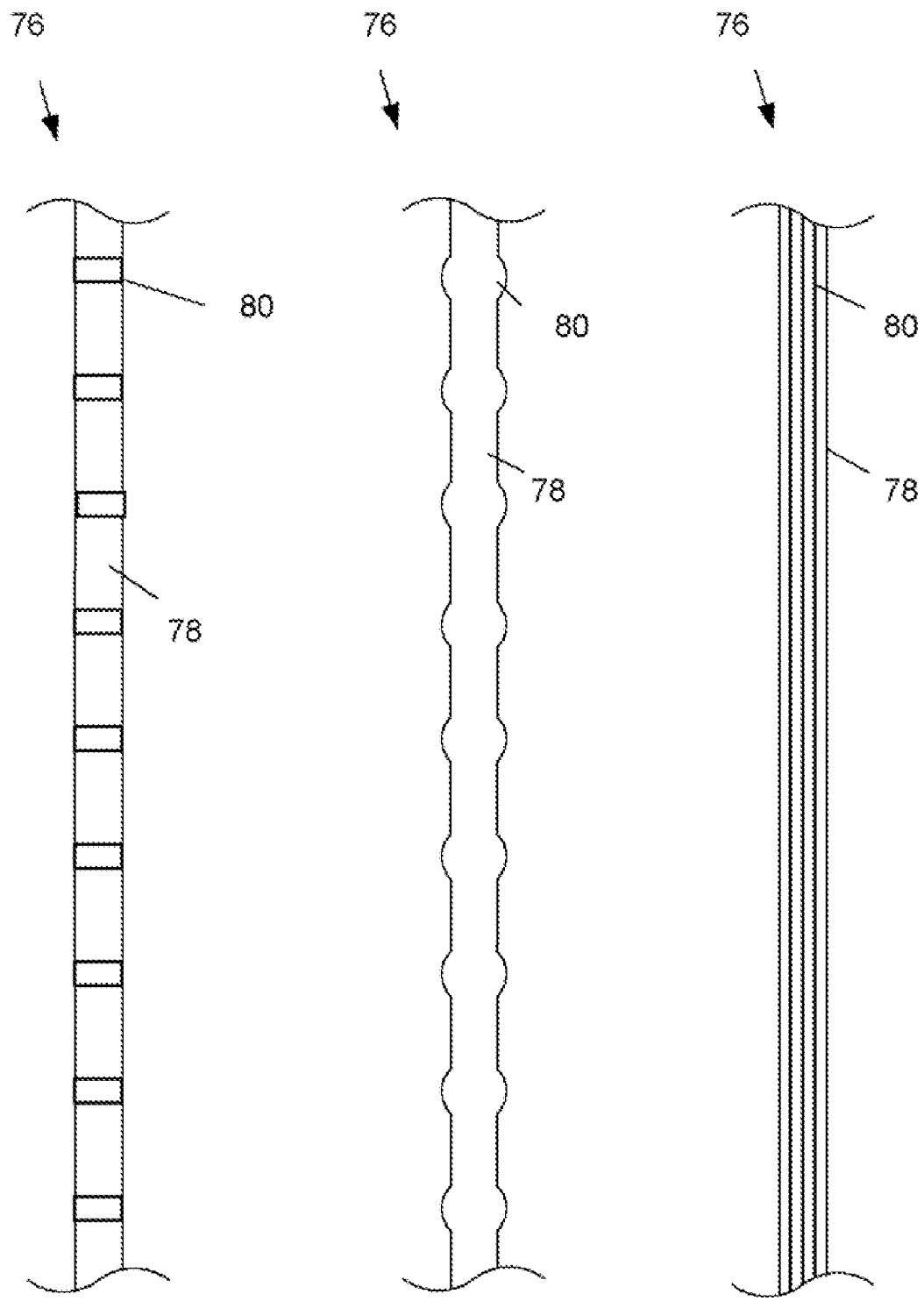

NOT INVENTION

NOT INVENTION

ANATOMICAL MEASUREMENT TOOL

CROSS-REFERENCE TO RELATED APPLICATION

This application is a continuation of PCT Application No. PCT/US 06/28239 filed 19 Jul. 2006 which claims priority to U.S. Provisional Application No. 60/700,359, filed 19 Jul. 2005, both of which are incorporated herein in its entirety.

BACKGROUND OF THE INVENTION

1. Field of the Invention

The invention is related to the measuring devices and measurement of anatomical pathologies.

2. Description of the Related Art

The ability to accurately measure the dimensions of anatomical structures is of vital importance. In many cases, the anatomical geometry defines the treatment. A small object, small hole, or short length of anatomical pathology can go untreated because it has little to no clinical significance. Larger objects, holes, and longer length of anatomical pathology may lead to adverse clinical outcomes.

Additionally, many anatomical pathologies are treated with devices, including implantable devices, that are sized to fit the pathology. Knowledge of the specific size of the pathology aids the selection of an appropriately sized treatment device. Using trial and error techniques to determine the proper size of an implantable treatment device undesirably prolongs the surgical procedure, and fitting and removing improperly sized devices often further traumatizes the already-injured anatomical site.

Existing devices do not easily measure tunnel defects in soft tissue within body structures. Tunnel defects can be found in the heart (e.g., patent foramen ovale (PFO), left atrial appendage, mitral valve prolapse, aortic valve defects). Tunnel defects can be found through out the vascular system (e.g., venous valve deficiency, vascular disease, vulnerable plaque, aneurysms (e.g., neurovascular, abdominal aortic, thoracic aortic, peripheral). Tunnel defects can be found in non vascular systems (e.g., stomach with GERD, prostate, lungs).

A device for measuring the width of a distended defect in tissue is disclosed. The device has a longitudinal axis. The device can have a first elongated member. The first elongated member can be configured to expand away from the longitudinal axis. The device can have a second elongated member. The first elongated member can be opposite with respect to the longitudinal axis to the second elongated member. The second elongated member can be configured to expand away from the longitudinal axis. The device can have a lumen, for example, in a catheter. The device can have a porous cover on the lumen.

A method for sizing a tunnel defect. The method can include inserting a measurement tool into the tunnel defect. The method can include distending the tunnel defect into a distended configuration. The method can include measuring the tunnel defect in the distended configuration. Distending can include radially expanding the measurement tool. Measuring can include bending the first measuring wire around a front lip of the tunnel defect. Measuring can include emitting a contrast fluid in the tunnel defect.

BRIEF SUMMARY OF THE INVENTION

Tissue distension devices can be deployed to tunnel defects in tissue. The tissue distension devices can be used to substantially close tunnel defects to treat, for example, patent foramen ovale (PFO), left atrial appendage, mitral valve prolapse, aortic valve defects. Examples of tissue distension devices include those disclosed in U.S. patent application Ser. Nos. 10/847,909, filed 19 May 2004; 11/184,069, filed 19 Jul. 2005; and 11/323,640, filed 3 Jan. 2006, all of which are incorporated by reference herein in their entireties.

To select a properly fitting tissue distension device, a measuring tool can first be deployed to measure the size of the tunnel defect. The tunnel defect can be measured in a relaxed or distended configuration. The tunnel defect can be distended by the measuring tool before or during measurement.

BRIEF DESCRIPTION OF THE DRAWINGS

FIGS. 5 through 8 illustrate variation s of the measurement tool in a second configuration.

FIGS. 20 through 23 illustrate variations of the measurement tool in a second configuration.

FIGS. 24 through 30 illustrate variations of the measuring wire.

DETAILED DESCRIPTION

Figure 1:
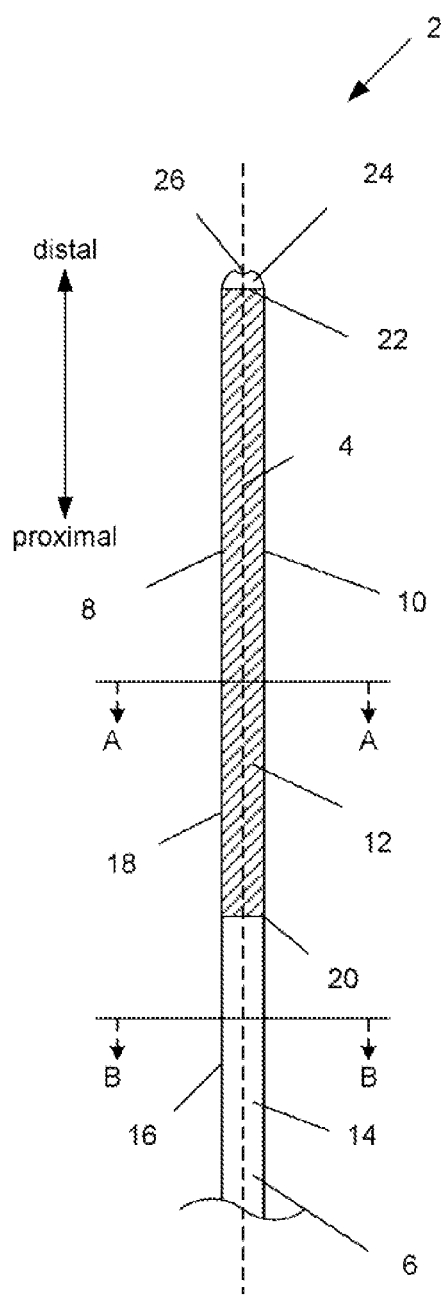
FIG. 1 illustrates a variation of the measurement tool in a first configuration.

FIG. 1 illustrates an anatomical measurement tool 2, such as a tool for measuring the width in a relaxed and/or distended configuration of a tunnel defect in tissue, in a radially contracted configuration. The measurement tool 2 can have a longitudinal axis 4. The anatomical measurement tool 2 can have a catheter 6, a first measuring wire 8, and a second measuring wire 10. The measuring wires 8 and 10 can be deformable, resilient, or combinations thereof over the length of the measuring wires.

The catheter 6 can have a catheter porous section 12. The catheter 6 can be entirely substantially non-porous. The catheter 6 can have a catheter non-porous section 14. The catheter porous section 12 can partially or completely circumferentially surround the catheter 6. The catheter porous section 12 can have holes or pores in the catheter outer wall 28. The pores can have pore diameters from about 10 μm (0.04 mil) to about 1 mm (0.04 in.), more narrowly from about 2 μm (0.08 mil) to about 300 μm (10 mil), for example about 150 μm (6.0 mil).

The first and second measuring wires 8 and 10 can each have at least one wire radially constrained section 16 and at least one wire radially unconstrained section 18. The measuring wires 8 and 10 can transition from the wire constrained sections to the wire radially unconstrained sections 18 at the wire proximal sheath ports 20. The first and second measuring wires 8 and 10 between the wire proximal sheath ports 20 and the wire distal anchor 22 can be the radially unconstrained sections. The measuring wires 8 and 10 can be distally fixed to the catheter 6 at a wire distal anchor 22. The wire distal anchor 22 can be a hinged or otherwise rotatable attachment, for example, to allow the measuring wire to rotate away from the longitudinal axis 4 at the wire distal anchor 22 during use.

The measurement tool 2 can have a tip 24 extending from a distal end of the catheter 6. The tip 24 can be blunt or otherwise atraumatic (e.g., made or coated with a softer material than the catheter 6, made with a soft substantially biocompatible rubber tip). A guide lumen 26 can extend from the tip 24. The guide lumen 26 can be configured to slidably receive a guidewire. The guide lumen 26 can have a guide lumen wall 27. The guide lumen 26 can exit through a dimple in the tip 24. The tip 24 need not be dimpled at the exit of the guide lumen 26.

Figure 2:
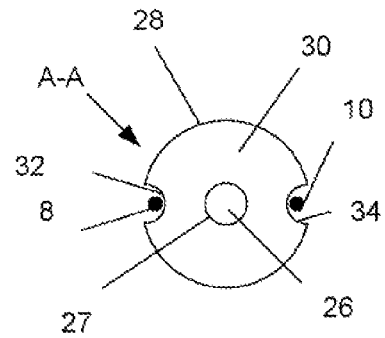
FIGS. 2 and 3 illustrate variation s of cross-section A-A of FIG. 1.

FIG. 2 illustrates that the catheter 6 can have a catheter outer wall 28. The catheter outer wall 28 can be porous, or non-porous, or partially porous and partially non-porous. The catheter 6 can have a fluid lumen 30. The guide lumen 26 can be configured central to the cross-section of the catheter 6 or offset from the center of the cross-section, for example attached to the catheter outer wall 28.

The first measuring wire 8 can removably and slidably reside in or removably and slidably attach to a recessed or raised first track 32 in the catheter outer wall 28. The second measuring wire 10 can removably and slidably reside in or removably and slidably attach to a recessed or raised second track 34 in the catheter outer wall 28.

To transform the measurement tool 2 from the radially contracted configuration to the radially expanded configuration, the first and second measuring wires 8 and 10 in the wire radially constrained section 16 can be longitudinally translated, as shown by arrows, in a distal direction. The first and second wires 8 and 10, for example, rotatably fixed at the wire distal anchor 22 and not radially constrained between the wire proximal sheath ports 20 and the wire distal anchor 22, can translate, as shown by arrows, radially outward from the longitudinal axis 4.

Figure 3:
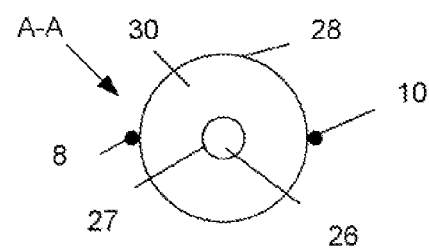

FIG. 3 illustrates that the first and second measuring wires 8 and 10 in the wire radially unconstrained section 18 can be adjacent to, and reside on or attach to, the catheter outer wall 28. The catheter outer wall 28 can have no tracks for the measuring wires.

Figure 4:
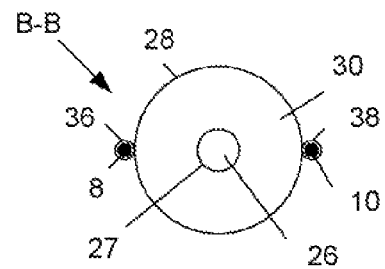
FIGS. 4 and 5 illustrate variation s of cross-section B-B of FIG. 1.

FIG. 4 illustrates that the first and second measuring wires 8 and 10 can be slidably attached to and/or encased by first 36 and second 38 sheaths, respectively. The interior of the sheaths can be coated with a low-friction material (e.g., polytetraflouroethylene (PTFE), such as Teflon® by E.I. du Pont de Nemours and Company, Wilmington, Del.).

Figure 5:
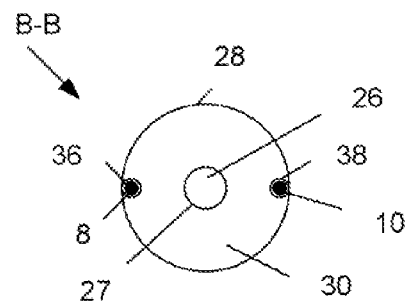

FIG. 5 illustrates that the first sheath 36 and/or the second sheath 38 can be inside the catheter 6 (i.e., radially interior to the catheter outer wall 28).

The wire distal anchor 22 and wire sheaths can be fixedly attached to the catheter 6. The wire distal anchor 22 and wire sheaths can be slidably attached to the catheter 6.

The catheter 6 and/or tip 24 can have stop. The stop can be longitudinally fixed with respect to the catheter 6 and/or the tip 24. The stop can be the tip 24, for example if the diameter of the tip 24 is larger than the diameter of the wire distal anchor 22. The stop can be configured to interference fit against the wire distal anchor 22 when the wire distal anchor 22 is distally translated beyond a maximum translation point with respect to the catheter 6 and/or tip 24.

Figure 6:
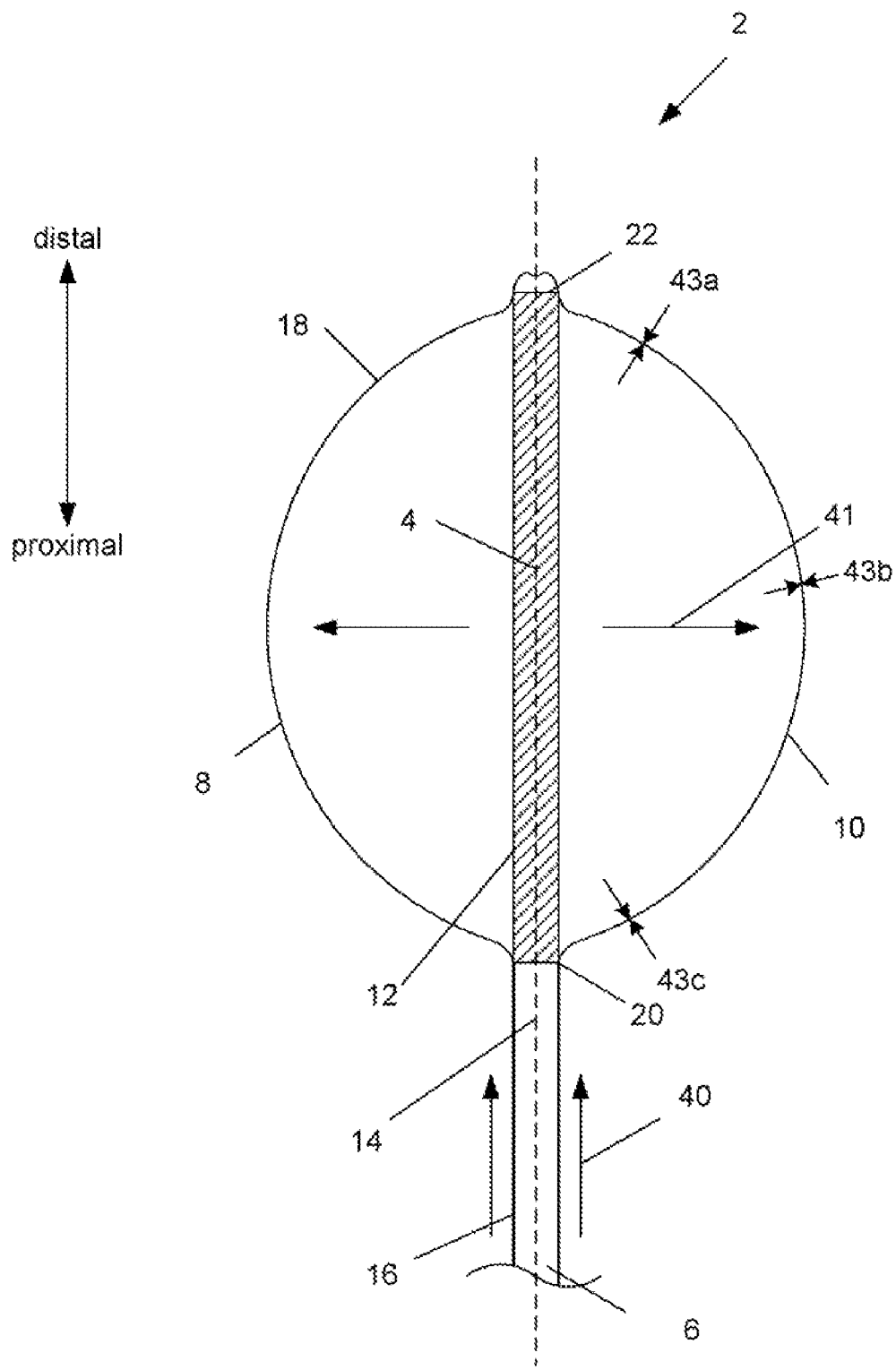

FIG. 6 illustrates the measurement tool 2 in a radially expanded configuration. The first and second measuring wires 8 and 10 in the wire radially unconstrained section 18 can bow, flex, or otherwise be radially distanced with respect to the longitudinal axis 4 from the catheter 6. The first and second 8 measuring wires 8 and 10 can expand in a single plane (i.e., coplanar).

The measuring wires 8 and 10 can be longitudinally translated, as shown by arrows 40, in the wire radially constrained sections 16. The first and second measuring wires 8 and 10 in the wire radially unconstrained sections 18 can be radially expanded or otherwise translated, as shown by arrows 41, away from the catheter 6 (e.g., longitudinal axis 4) into a radially expanded configuration, for example by distally translating the measuring wires 8 and 10 in the wire radially constrained sections 16. The first and second measuring 8 and 10 wires in the wire radially unconstrained sections 18 can be radially contracted or otherwise translated toward the catheter 6 (e.g., longitudinal axis 4) into a radially contracted configuration, for example by proximally translating the measuring wires 8 and 10 in the wire radially constrained section 16.

The measuring wires 8 and 10 can have wire first diameters 43a, wire second diameters 43b, and wire third diameters 43c. In the radially expanded configuration, the wire first diameters 43a can be adjacent to the wire distal anchor 22. In the radially expanded configuration, the wire second diameters 43b can be substantially half-way along the wire length between the wire distal anchor 22 and the wire proximal sheath port 20. In the radially expanded configuration, the wire third diameters can be adjacent to the proximal sheath port 20. The wire first diameter 43a can be substantially equal to the wire third diameter 43c. The wire second diameter 43b can be less than, greater than, or equal to the wire first diameter 43a and/or the wire third diameter 43c.

Figure 7:
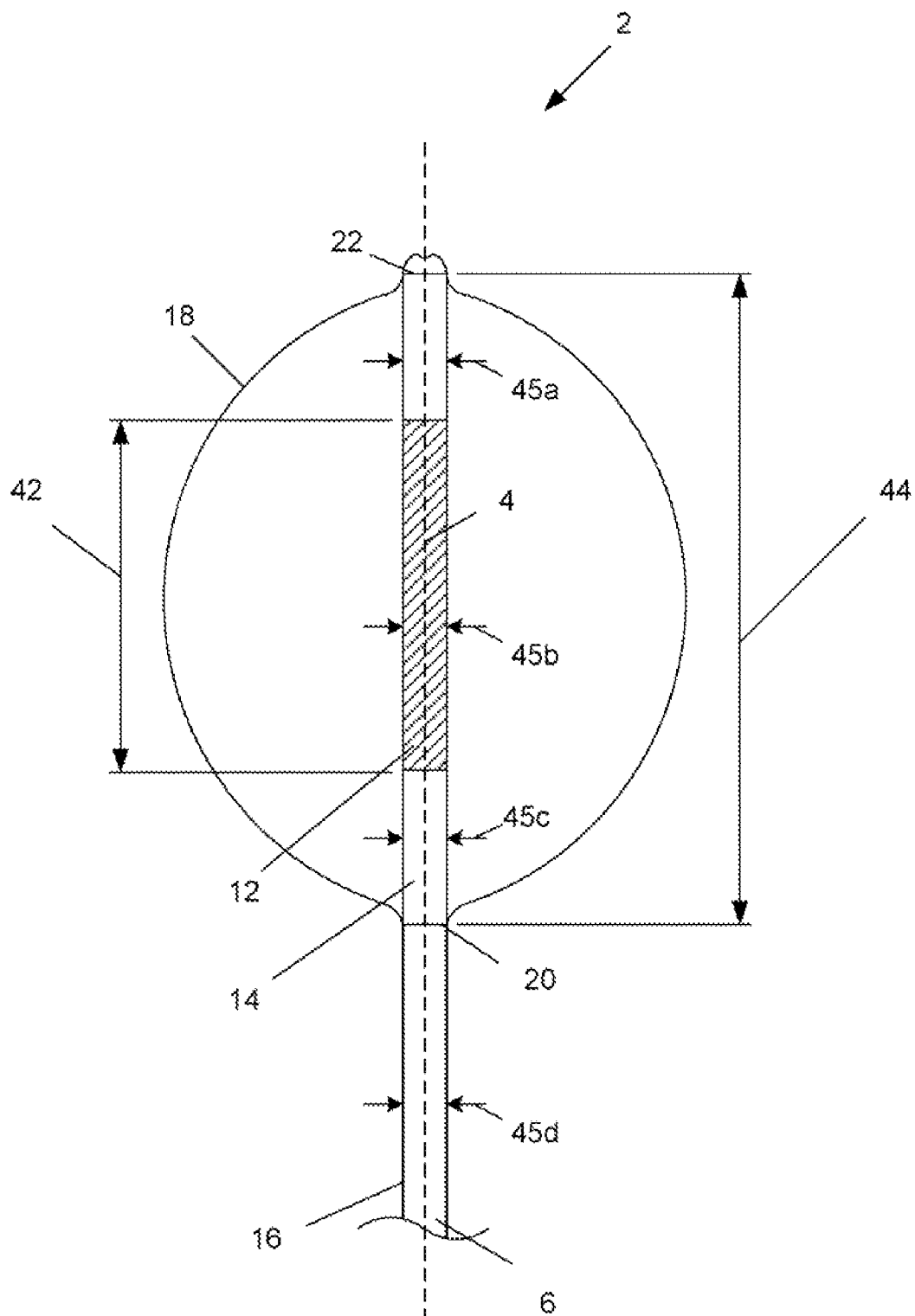

FIG. 7 illustrates that the catheter porous section 12 can have a porous section length 42. The longitudinal distance between the wire distal anchor 22 and the wire proximal sheath ports 20 (i.e., the wire radially unconstrained section 18) can be an unconstrained wire longitudinal length 44. The unconstrained wire longitudinal length 44 can be less than, substantially equal to (as shown in FIGS. 1 and 6), or greater than (as shown in FIG. 7) the catheter non-porous section 14.

The catheter 6 can have a catheter first diameter 45a, a catheter second diameter 45a, a catheter third diameter 45a, and a catheter fourth diameter 45a. The catheter first diameter 45a can be adjacent to the wire distal anchor 22 and/or otherwise between the catheter porous section 12 and the wire distal anchor 22. The catheter second diameter 45b can be at the catheter porous section 12. The catheter third diameter 45c can be adjacent to the wire proximal sheath 20 and/or otherwise between the catheter porous section 12 and the wire proximal sheath port 20. The catheter fourth diameter 45d can be proximal to the wire proximal sheath port 20.

The catheter first diameter 45a can be substantially equal to the catheter third diameter 45c. The catheter second diameter 45b can be less than, greater than, or equal to the catheter first section 45*a* and/or the catheter third section 45*c*. The catheter fourth section 45*d* can be less than, greater than, or equal to the catheter first diameter 45*a* and/or catheter second diameter 45*b* and/or catheter third diameter 45*c*.

Figure 8:
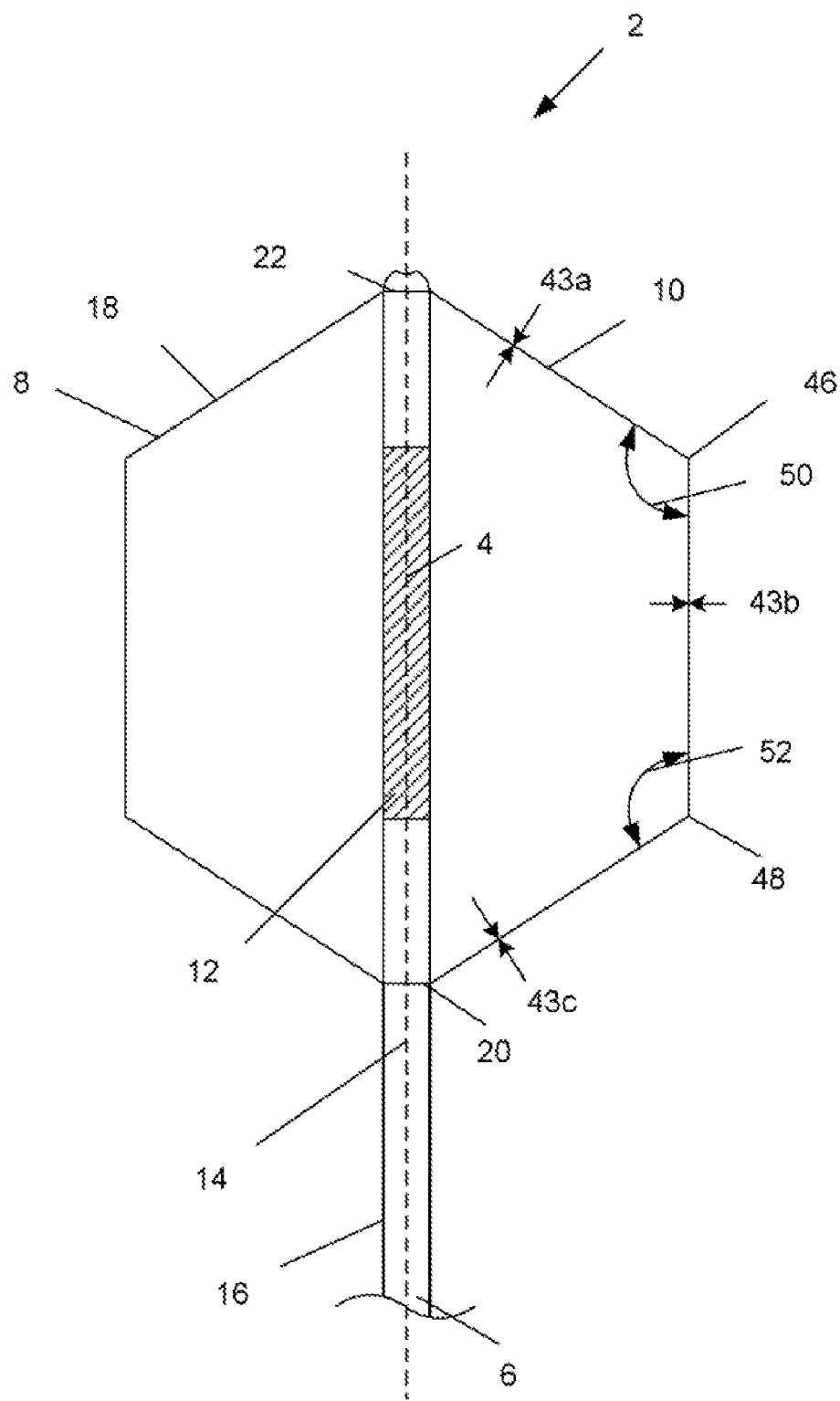

FIG. 8 illustrates that the first and second wires can have substantially discrete angles when the wires are in the radially expanded configurations. Each wire can have a wire first hinge point 46 and a wire second hinge point 48. The wire hinge points can be biased (e.g., before the measurement tool 2 is configured in the first configuration) to bend when the tension on the measuring wire is decreased. The wire hinge points can have hinges, bends, seams, links, other articulations, or combinations thereof.

The wire first hinge point 46 can have a wire first hinge angle 50. The wire second hinge point 48 can have a wire second hinge angle 52. In a radially expanded configuration, the wire hinge first and second angles can be from about 10° to about 170°, more narrowly from about 30° to about 150°, yet more narrowly from about 45° to about 135°, for example about 125°.

Figure 9:
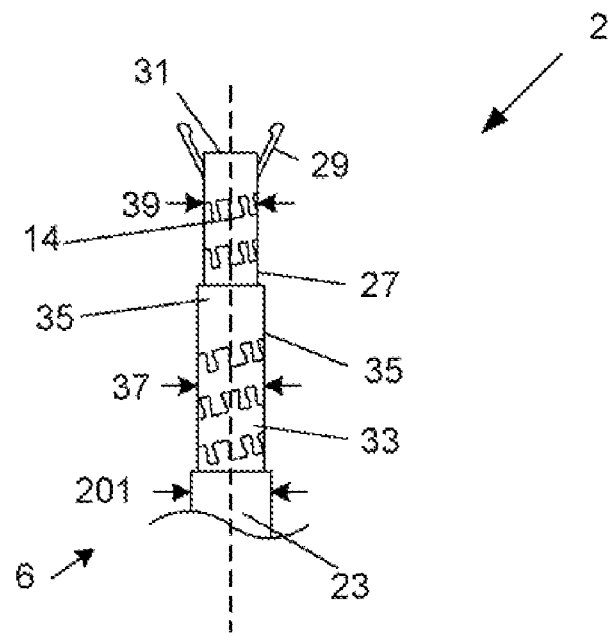
FIG. 9 illustrates a variation of the measurement tool in a first configuration in a first configuration.

FIG. 9 illustrates that the catheter 6 can have an inner tube 27, and/or an outer tube 25, and/or a catheter exterior 23. The inner tube 27 can be slidably or fixedly attached to the outer tube 25. The outer tube 25 can be slidably or fixedly attached to the catheter exterior 23. The inner tube 27, and/or the outer tube 25, and/or the catheter exterior 23 can be flexible or rigid.

The inner tube 27 can have forceps or rails 29 extending therefrom. The rails 29 can be rigid or flexible. The rails 29 can be rotationally and/or translatably attached to the inner tube 27. The rails 29 can be configured to guide the measuring wires 8 and 10, for example as the measuring wires 8 and 10 deploy, and/or to attach to or otherwise grab the measuring wires 8 and 10 and/or to attach to or otherwise grab a separate implant, such as a previously deployed embolic filtering device, and/or to grab tissue.

The distal end of the inner tube 27 can have a deployment port 31.

The inner tube 27, and/or the outer tube 25, and/or the catheter exterior 201 can be made from one or more flexibly connected, interlocking elements. For example, the interlocking elements can be spiral cut. The interlocking elements can be tube mid components 33 and/or tube end components 35. The tube end component of the inner tube 27 can have the deployment port 31.

The catheter exterior 23 can have a catheter exterior diameter 201. The outer tube 25 can have an outer tube diameter 33. The inner tube 27 can have an inner tube diameter 39. The catheter exterior diameter 201 can be greater than or less than the outer tube diameter 33. The outer tube diameter 33 can be greater than or less than the inner tube diameter 39. The inner tube diameter 39 can be greater than or less than the catheter exterior diameter 201.

Figure 10:
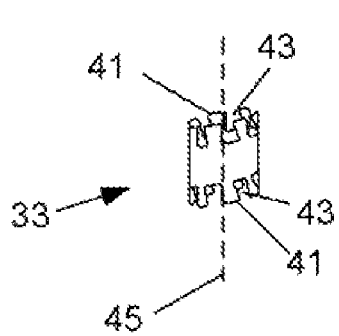
FIGS. 10 and 11 illustrate variations of interlocking element component.

FIG. 10 illustrates that the tube mid component 33 can have an element longitudinal axis 45. The element longitudinal axis 45 can be perpendicular or at an angle to a plane formed by either longitudinal end of the tube mid-component 33. The tube mid component 33 can have angularly alternating male interlocking elements 41 and female interlocking elements 43 around each longitudinal end of the tube mid component 33. The male interlocking elements 41 can be configured to fixedly or releasably, and/or rotatably attach to the female interlocking elements 43.

Figure 11:
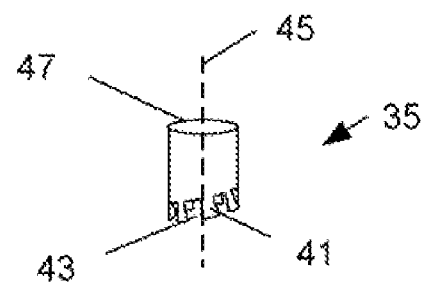

FIG. 11 illustrates that the tube end component 35 can have a tube end port 47 at least at one longitudinal end of the tube end component 35. The tube end port 47 can have no interlocking elements. The tube end port 47 can form a plane parallel or at an angle to the element longitudinal axis 45.

Figure 12:
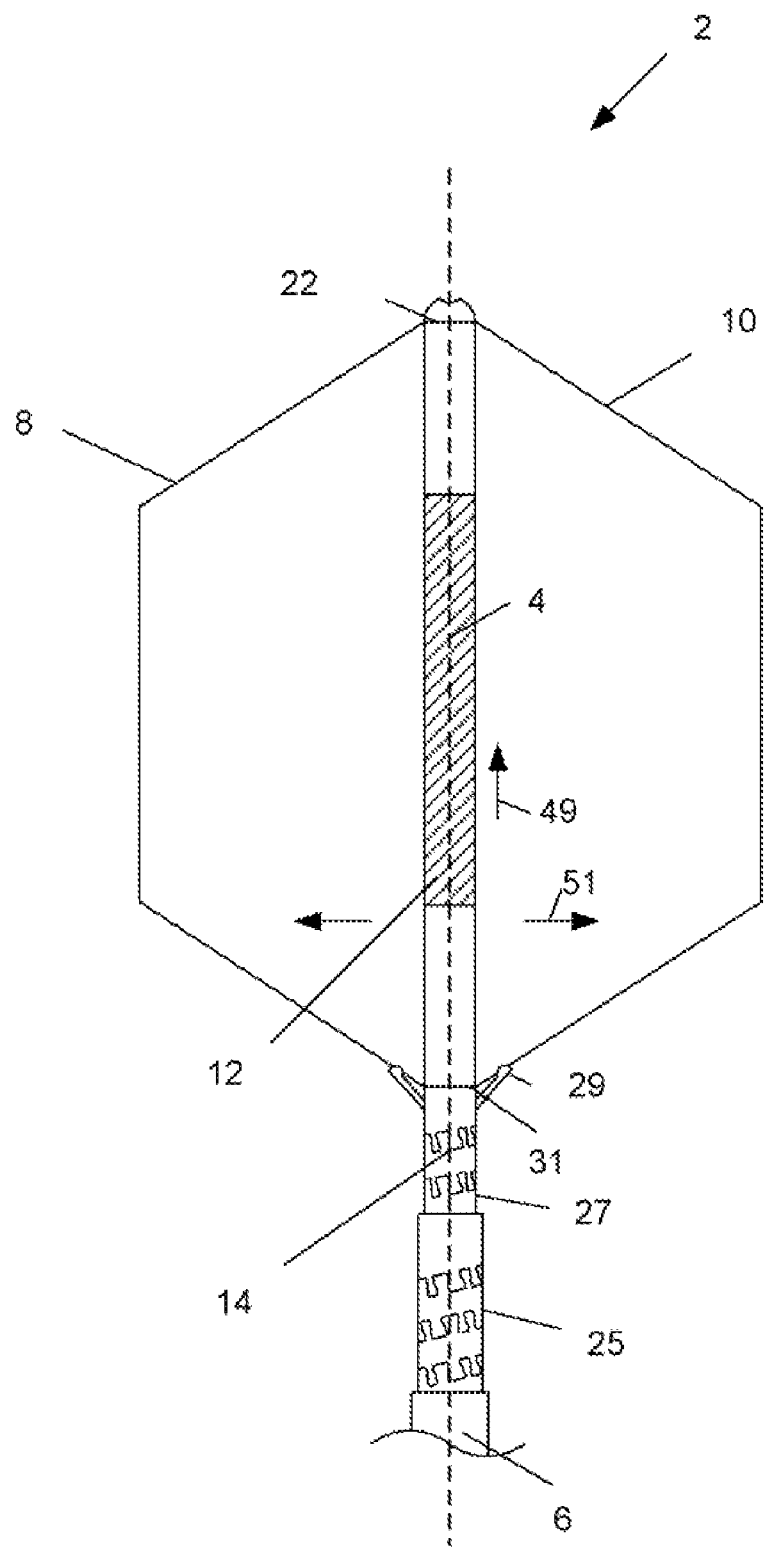
FIG. 12 illustrates the variation of the measurement tool of FIG. 9 in a second configuration.

FIG. 12 illustrates that as the measurement tool 2 transforms from the first configuration of the second configuration, the remainder of the catheter 6 can translate, as shown by arrow 49, out of the end of the deployment port 31. The measuring wires 8 and 10 can resiliently radially expand, as shown by arrows 51, when released from the deployment port 31. The measuring wires 8 and 10 can be deformably radially expand, as shown by arrows 51, by an external force.

Figure 13:
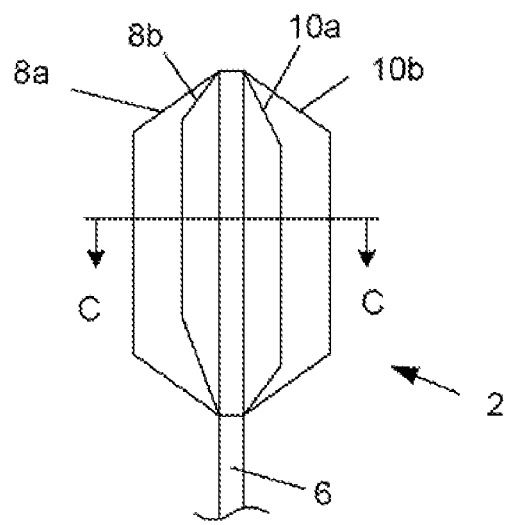
FIG. 13 illustrates a side view of variation of the measurement tool in a second configuration.
Figure 14:
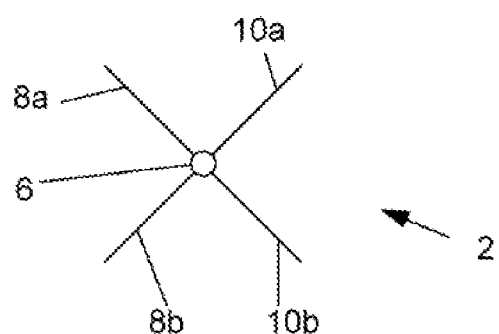
FIG. 14 illustrates a top view of the measurement tool of FIG. 13.
Figure 15:
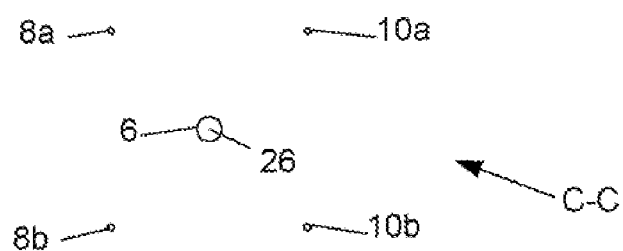
FIG. 15 illustrates a variation of cross-section C-C of the measurement tool of FIG. 13.

FIGS. 13 through 15 illustrate that the measurement tool 2 can have four or more measuring wire 8*a*, 8*b*, 10*a* and 10*b*. In a radially expanded configuration, the measuring wires can extend from the catheter 6 in substantially opposite directions. For example, the first measuring wire 8*a* can extend substantially opposite to the fourth measuring wire 10*b*. The second measuring wire 10*a* can extend substantially opposite to the third measuring wire 8*b*. The angle between each measuring wire can be about 90°. Three or more than four measuring wires can be used and the angle between measuring wires can be from about 0° to about 350°, more narrowly from about 30° to about 180°, for example about 45°.

Figure 16:
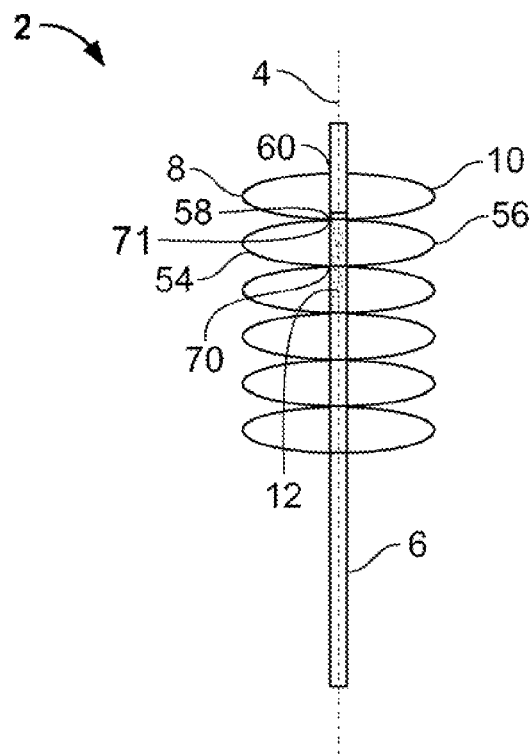
FIGS. 16 through 18 illustrate variations of the measurement tool in a second configuration.

FIG. 16 illustrates that the measurement tool 2 can have about 12 measuring wires. The measuring wires can be radially expandable in a configuration where the first measuring wire 8 deploys substantially longitudinally adjacent to a third measuring wire 54. The measuring wires can be radially expandable in a configuration where the second measuring wire 10 deploys substantially longitudinally adjacent to a fourth measuring wire 56.

The measuring wires can each have a unique or paired longitudinal position for their wire proximal sheath ports 20 and wire distal anchors 22. For example, the first and second measuring wires 8 and 10, respectively, can exit from wire first proximal sheath ports 58 and can be fixed at wire first distal anchors 60. The third and fourth measuring wires 54 and 56, respectively, can exit from one or two wire second proximal sheath ports 70 and can be fixed at one or two wire second distal anchors 71. The wire first distal anchors 60 can be distal to the wire second distal anchors 71. The wire first proximal sheath ports 58 can be at a substantially equivalent longitudinal position to the wire second distal anchors 71. The wire second distal anchors 71 can be distal to the wire second proximal sheath ports 70. This longitudinal spacing of the wire distal anchors 22 and wire proximal sheath ports can be used for all of the measuring wires.

The measuring wires on each side of the catheter 6 (e.g., the first, third, fifth, seventh, ninth and eleventh measuring wires or the second, fourth, sixth, eighth, tenth and twelfth measuring wires) can pass through the same or different sheaths.

Figure 17:
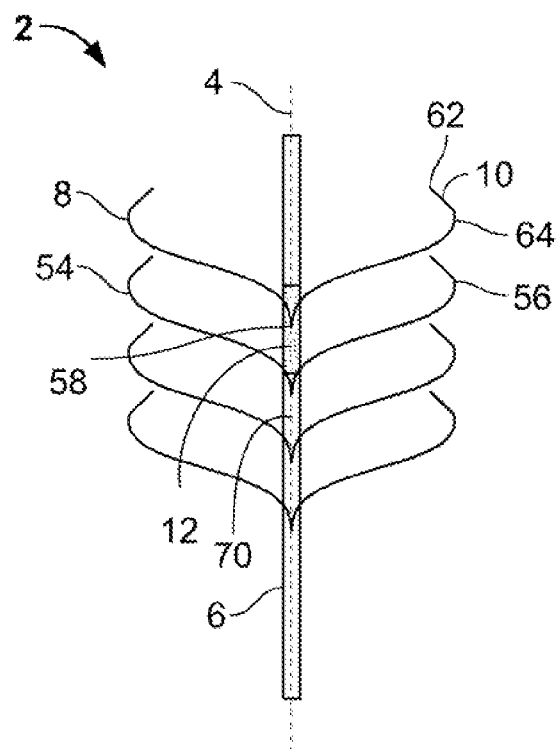

FIG. 17 illustrates that the measuring wires can have distal ends that are not attached to the catheter 6 when the measuring wires are in radially expanded configurations. Any or all measuring wire can have a terminal end 62. When the measurement tool 2 is in a radially expanded configuration, the terminal ends 62 can be unattached to the catheter 6. When the measurement tool 2 is in a radially expanded configuration, the measuring wires can have a medial turn 64, bend, hinge, or otherwise angle medially between the terminal ends 62 and the wire proximal ports. A length of the measuring wires can be biased to turn or bend medially when that length of the measuring wire is in a relaxed configuration. The measurement tool 2 can have about eight measuring wires.

Figure 18:
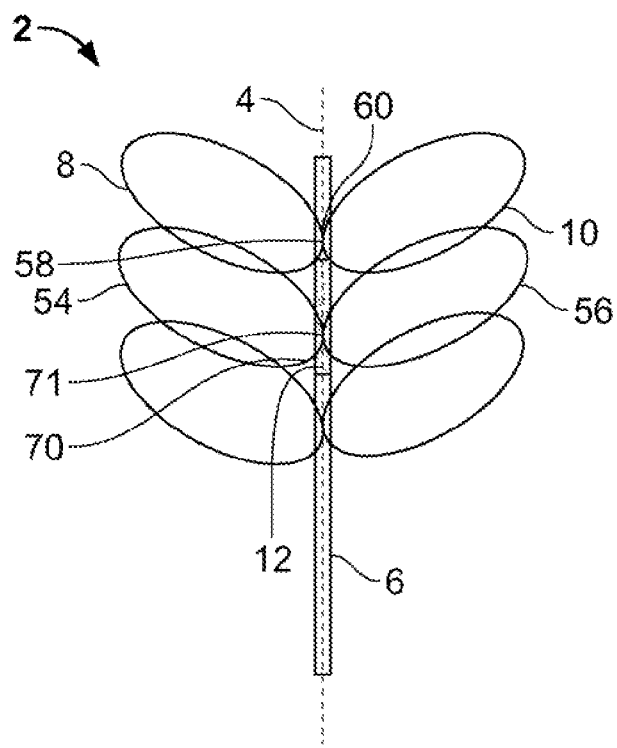

FIG. 18 illustrates that the measuring wires can form a substantially circular or oval loop when the measuring wire is in the radially expanded configuration. The measurement tool 2 can have six measuring wires.

Figure 19:
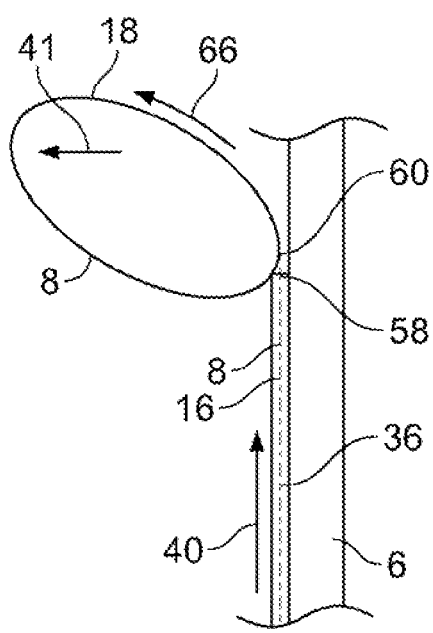
FIG. 19 is a close-up view of the a portion of the measurement tool of FIG. 18 including the first measuring wire only, for illustrative purposes, transforming from a radially contracted to a radially expanded configuration.

FIG. 19 illustrates that the loop of wire radially unconstrained section 18 can expand when the measuring wires transform from the radially contracted configuration to the radially expanded configuration. The measuring wires can be longitudinally translated, as shown by arrows 40, in the wire radially constrained sections 16. Along the length of the measuring wires near the wire proximal port, the measuring wires can translate along the longitudinal wire-axis, as shown by arrow 66. The measuring wires in the wire radially unconstrained sections 18 can be radially expanded or otherwise translated, as shown by arrow, away from the catheter 6 (e.g., longitudinal axis 4) into a radially expanded configuration, for example by distally translating the measuring wires in the wire radially constrained sections 16. The measuring wires in the wire radially unconstrained sections 18 can be radially contracted or otherwise translated toward the catheter 6 (e.g., longitudinal axis 4) into a radially contracted configuration, for example by proximally translating the measuring wires in the wire radially constrained section 16.

Figure 20:
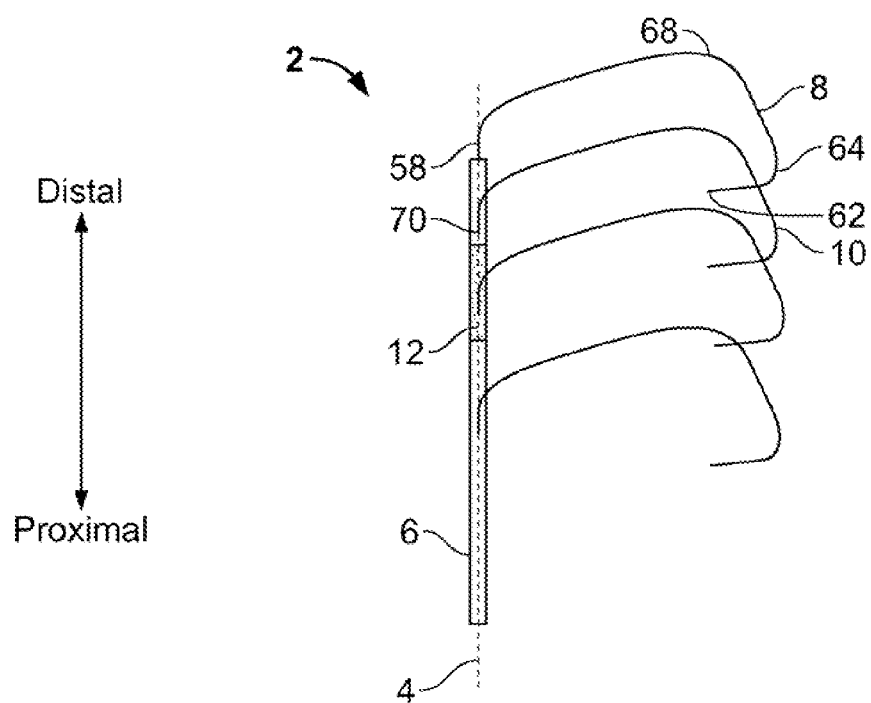
Figure 21:
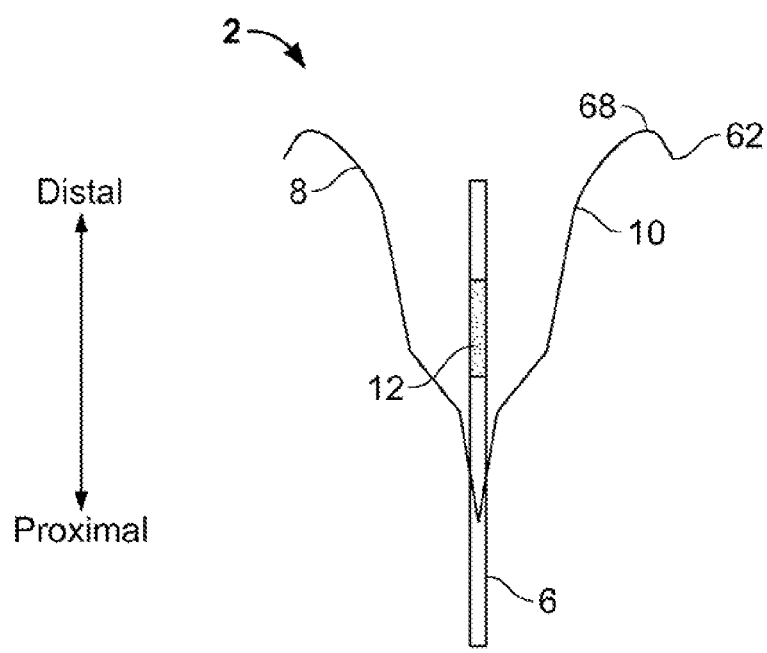

FIG. 20 illustrates that the measuring wires can exit from the respective wire sheaths at the respective wire proximal pores. The measuring wires can all exit the wire proximal ports on the same side of the catheter 6, or immediately turn to the same side of the catheter 6 after exiting the proximal wire ports. When the measurement tool 2 is in a radially expanded configuration, the measuring wires can have a proximal turn 68, bend, hinge, or otherwise angle proximally after exiting the proximal wire port. When the measurement tool 2 is in a radially expanded configuration, the measuring wires can have a medial turn 64, bend, hinge, or otherwise angle toward the longitudinal axis 4, for example, between the proximal bend 68 and the terminal end 62. Any length of the measuring wires can be biased to turn or bend when that length of the measuring wire is in a relaxed configuration. FIG. 21 illustrates that the measuring wire can have a proximal turn 68, bend, hinge, or otherwise angle proximally.

FIG. 22 illustrates that the catheter 6 can be removably or fixedly attached to a coupler 72. The coupler 72 can be removably or fixedly attached to a handle 74. The coupler 72 can be made from any material disclosed herein including rubber, elastic, or combinations thereof. The coupler 72 can have a substantially cylindrical configuration. The coupler 72 can have threads. The coupler 72 can have slots. The coupler 72 can have a joint or hinge. The coupler 72 can be flexible or rigid. The coupler 72 can be resilient or deformable.

The coupler 72 can be flexible. The coupler 72 can substantially bend, for example, permitting the longitudinal axis 4 of the handle 74 to be a substantially non-zero angle (e.g., from about 0° to about 90° C.) with respect to the longitudinal axis 4 of the catheter 6. The coupler 72 can permit substantially resistance free rotation between the longitudinal axis 4 of the catheter 6 and the longitudinal axis 4 of the handle 74.

FIG. 23 illustrates that the coupler 72 can be removably or fixedly attached to the catheter 6 on the proximal and distal end of the coupler 72. The coupler 72 can have and/or be proximally adjacent to the wire proximal sheath ports 20.

Figure 24:
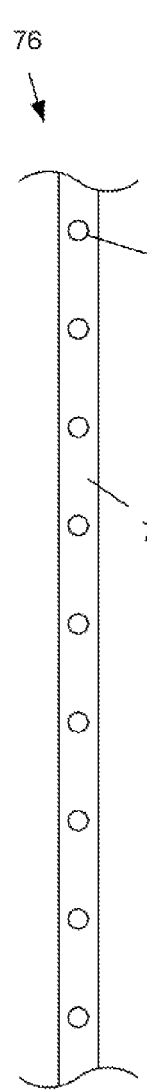

FIG. 24 illustrates that the measuring wire 76 can have a wire body 78 and one or more markers 80. The wire body 78 can have no markers 80. The markers 80 can be echogenic, radiopaque, magnetic, or configured to be otherwise visible by an imaging technique known to one having ordinary skill in the art. The markers 80 can be made from any material disclosed herein including platinum (e.g., pure or as powder mixed in glue).

Figure 25:
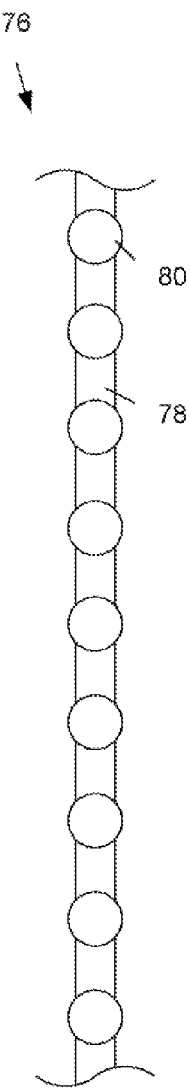

The markers 80 can be uniformly and/or non-uniformly distributed along the length of the wire body 78. The markers 80 can be uniformly and/or non-uniformly distributed along the radius of the wire body 78. The markers 80 can be separate and discrete from the wire body 78. The markers 80 can be attached to the wire body 78. The markers 80 can be incorporated inside the wire body 78. The marker 80 can have configuration symmetrical about one, two, three, or more axes. The marker 80 can have an omnidirectional configuration. The marker 80 can have a configuration substantially spherical, ovoid, cubic, pyramidal, circular, oval, square, rectangular, triangular, or combinations thereof. The marker's radius can be smaller than or substantially equal to the wire body's radius at the location of the marker 80. FIG. 25 illustrates that the marker's radius can be greater than the wire body's radius at the location of the marker 80.

Figure 26:
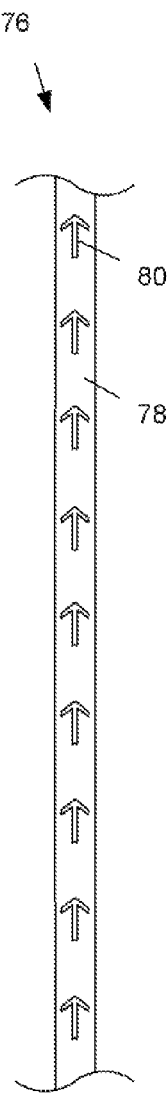

FIG. 26 illustrates that the marker 80 can have a unidirectional configuration. The marker 80 can be configured in the shape of an arrow. All or subsets of the markers 80 on a wire body 78 can be aligned, for example all of the unidirectionally configured markers 80 can be oriented in the same longitudinal or radial direction (e.g., distally, proximally) along the wire body 78.

Figure 27:
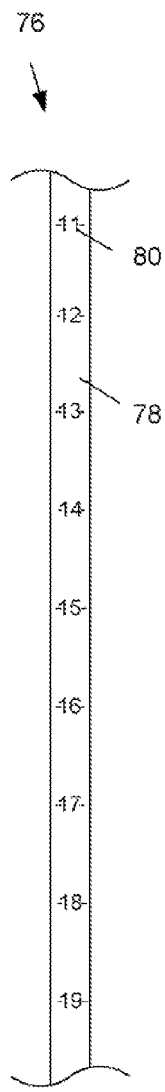

FIG. 27 illustrates that the markers 80 can have alphanumeric characters. The alphanumeric characters can increase in value (e.g., 1, 2, 3, or A, B, C, or I, II, III) incrementally along the length and/or radius of the wire. The markers 80 can include unit values (e.g., mm, in.)

FIG. 28 illustrates that the markers 80 can be configured as a cylinder (e.g., disc), ring (e.g., toroid, band), partial cylinder, partial ring, or combinations thereof. FIG. 29 illustrates that the markers 80 can be integrated with the measuring wire 76. FIG. 30 illustrates that the markers 80 can be wires or threads. The markers 80 can extend along the length and/or radius of the wire body 78.

Any or all elements of the measurement tool 2 and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, Del.), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeyvell International, Inc., Morris Township, N.J., or DYNEEMA® from Royal DSM N. V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thennedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold. For example, the measuring wires 8 and 10, and/or any other element of the measuring tool 2 can have tantalum and/or be wrapped with or otherwise attached to tantalum ribbon.

Any or all elements of the measurement tool 2 and/or other devices or apparatuses described herein, can be, have, and/or be completely or partially coated with agents and/or a matrix a matrix for cell ingrowth or used with a fabric, for example a covering (not shown) that acts as a matrix for cell ingrowth. The matrix and/or fabric can be, for example, polyester (e.g., DACRON® from E. I. Du Pont de Nemours and Company, Wilmington, Del.), polypropylene, PTFE, ePTFE, nylon, extruded collagen, silicone or combinations thereof.

The measurement tool 2 and/or elements of the measurement tool 2 and/or other devices or apparatuses described herein and/or the fabric can be filled, coated, layered and/or otherwise made with and/or from cements, fillers, glues, and/or an agent delivery matrix known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rhBMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and Chlamydia Pneumoniae, *Brit. J. Surgery* 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

Methods of Use

Figure 31:
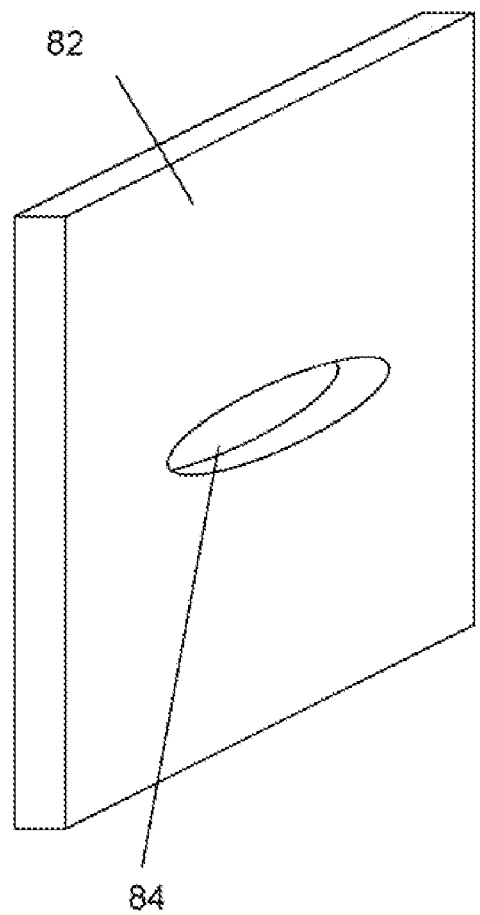
FIG. 31 illustrates a section of tissue having a tunnel defect.
Figure 32:
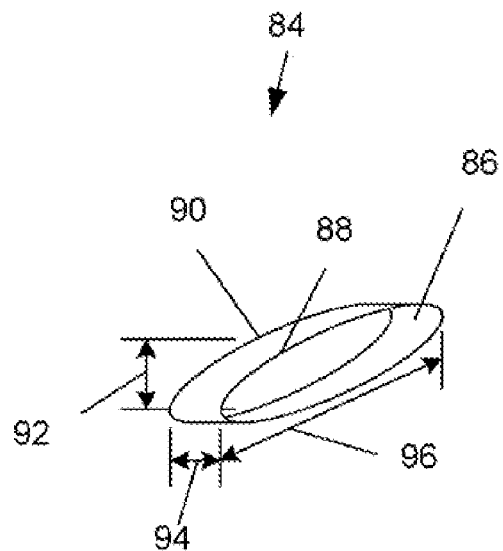
FIG. 32 illustrates the tunnel defect of FIG. 31.

FIG. 31 illustrates a section of tissue 82 that can have a tunnel defect 84 passing through the tissue 82. FIG. 32 illustrates that the tunnel defect 84 can have a defect front face 86 and a defect back face (not shown). A defect front lip 88 can be defined by the perimeter of the defect front face 86. A defect back lip 90 can be defined by the perimeter of the defect back face. The tunnel defect 84 can have a defect height 92, a defect depth 94 and a defect width 96.

Figure 33:
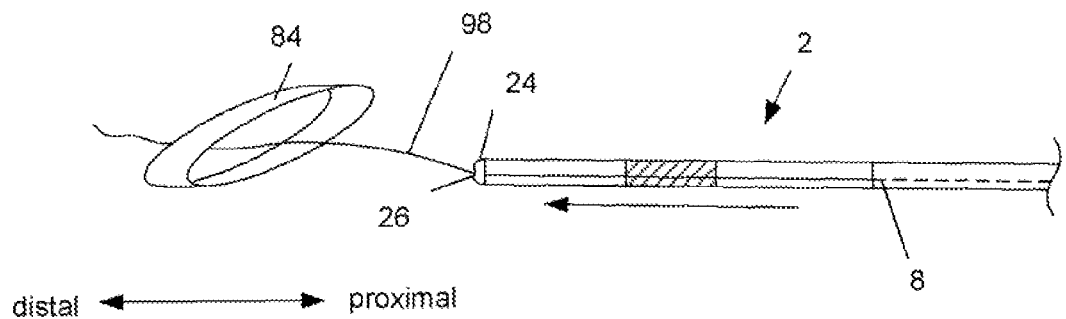
FIGS. 33 through 35 illustrate a variation of a method for deploying an embodiment of the measurement tool.

FIG. 33 illustrates that a guidewire 98 can be deployed through the tunnel defect 84. The guidewire 98 can be passed through the guide lumen 26 in the measurement tool 2. The measurement tool 2 can be in a radialy contracted (as shown) or radially expanded configuration. The measurement tool 2 can be translated, as shown by arrow, along the guidewire 98. The measurement tool 2 can be translated to the tunnel defect 84 with or without the use of the guidewire 98.

Figure 34:
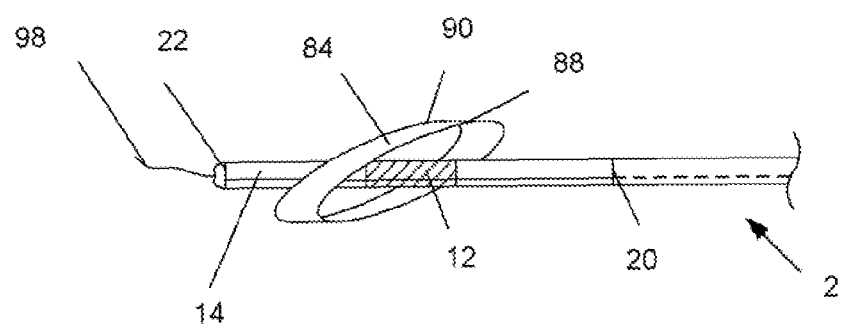

FIG. 34 illustrates that the measurement tool 2 can be translated into the tunnel defect 84. The guidewire 98 can be left in place or removed. The location of the measurement tool 2 can be monitored by dead reckoning, and/or imaging, and/or tracking along the length of the guidewire 98. The measurement tool 2 can be positioned so that the tunnel defect 84 is located adjacent to the catheter porous section 12. The measurement tool 2 can be positioned so that the tunnel defect 84 is located substantially between the most distal wire distal anchor 22 and the most proximal wire proximal sheath.

Figure 35:
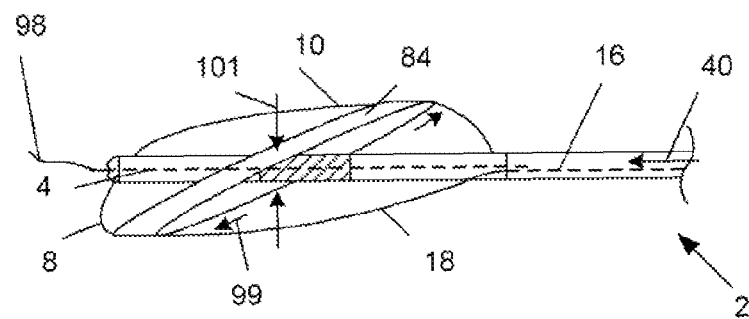

FIG. 35 illustrates that the measurement tool 2 can be radially expanded. The measuring wires in the wire radially constrained section 16 can be distally longitudinally translated. The measuring wires 8 and 10 can translate radially (i.e., away from the longitudinal axis 4). The measuring wires 8 and 10 can radially distend the tunnel defect 84, for example causing the tunnel defect 84 to widen, as shown by arrows 99, and shorten (i.e., contract height-wise), as shown by arrows 101. The measuring wires 8 and 10 can radially distend the tunnel defect 84, for example, until the tunnel defect 84 will no longer distend without structurally damaging the tunnel defect 84.

Figure 36:
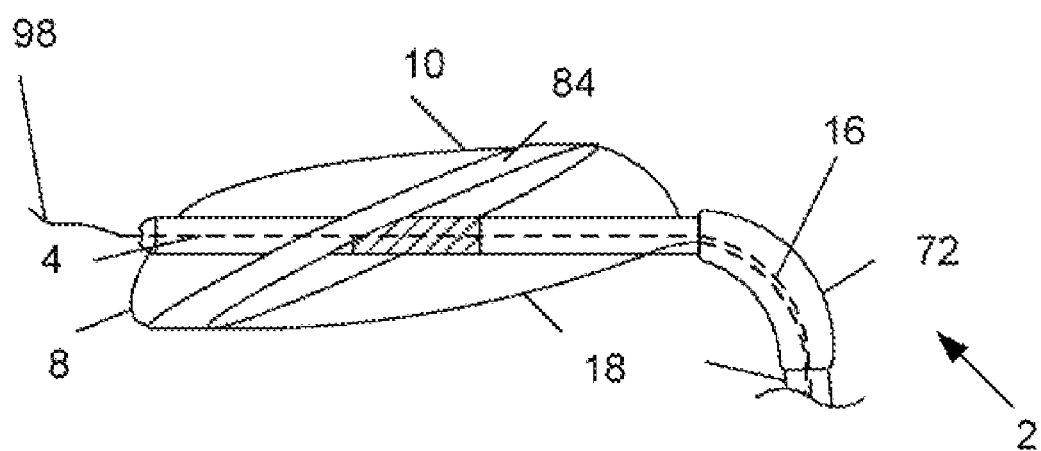
FIGS. 36 through 39 illustrate variations of methods for using variations of the measurement tool.

FIG. 36 illustrates that the coupler 72 can bend, for example to maintain substantially plane of the tunnel defect 84 and the longitudinal axis 4 at the location where the measurement tool 2 passes through the tunnel defect 84. The coupler 72 can disengage at the coupler's distal (or proximal) end, for example, leaving the distal end of the measurement tool 2 in the tunnel defect 84. The distal end of the measurement tool 2 can then be used, for example, to distend the tunnel defect 84 to substantially close and treat the tunnel defect 84.

Figure 37:
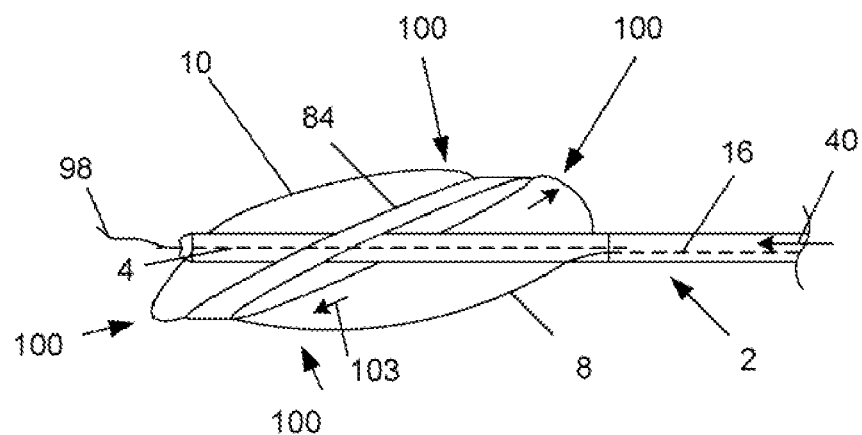

FIG. 37 illustrates that the measuring wires can be radially translated, as shown by arrows 103, beyond the extent that the tunnel defect 84 can be distended without structural damage. The measuring wires 8 and 10 can deform around the front and back defect lips. Portions of the measuring wires can configure into wire overdeployment sections 100 proximal and distal to the tunnel defect 84. The wire overdeployment sections 100, or markers 80 thereon, can be imaged, for example using x-rays (e.g., radiography, fluoroscopy), ultrasound, or magnetic resonance imaging (MRI). The wire overdeployment sections 100 can illustrate the defect width 96 (i.e., the length between the wire deployment sections) when the defect is in a fully distended configuration.

Figure 38:
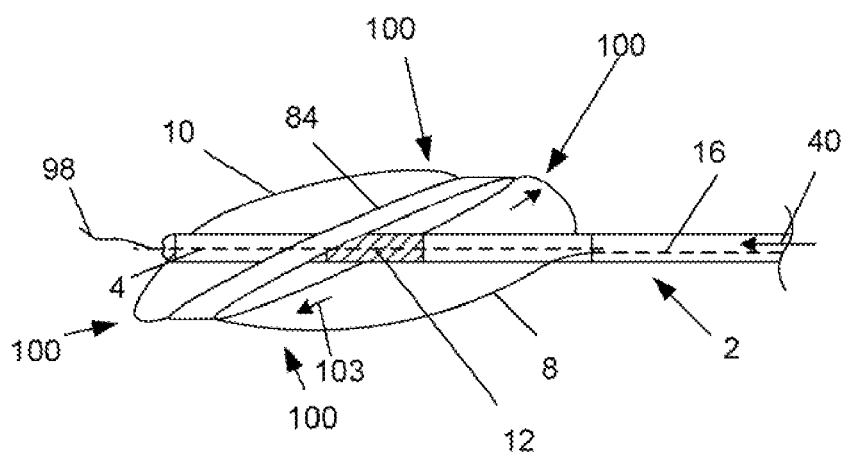

FIG. 38 illustrates that the measurement tool 2 can have no catheter porous section 12, for example, when the measurement tool 2 is used for the measurement method as shown in FIG. 37. The methods of use shown in FIGS. 37 and 38 can, for example, measure the defect depth 94 and/or the defect height 92.

The measuring tool 2 of FIGS. 13 through 15 can be used to distend and measure the tunnel defect 84 in more than one plane concurrently, and/or alternately in quick succession.

Figure 39:
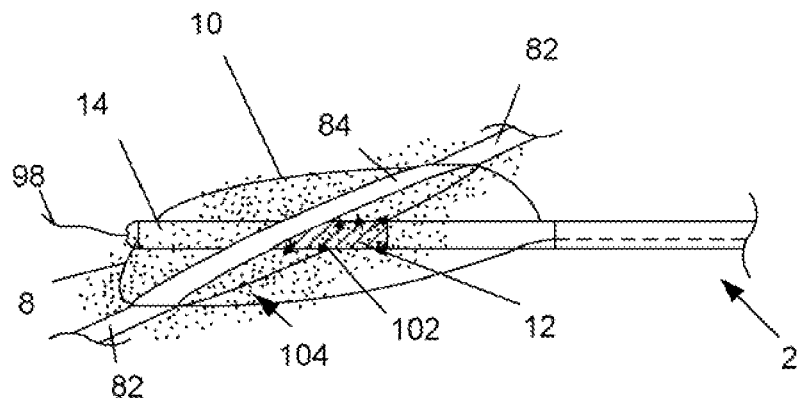

FIG. 39 illustrates that contrast fluid or particles can be deployed into the fluid lumen 30 of the catheter 6, for example, when tunnel defect 84 is in a fully distended configuration. The contrast fluid can be radiopaque, echogenic, visible contrast (e.g., dyes, inks), any other material disclosed herein, or combinations thereof. The fluid pressure of the contrast fluid or particles can be increased. The contrast fluid or particles can emit, as shown by arrows 102, through the catheter porous section 12. The contrast fluid or particles outside of the catheter 6 can configure into a marker cloud 104. The marker cloud 104 can move into position around the tissue 82. The marker cloud 104 can illustrate the defect dimensions (i.e., visible with imaging systems known to those having ordinary skill in the art, including x-ray, CAT, MRI, fiber optic camera, ultrasound/sonogram) when the defect is in a fully distended configuration.

A drug can be deployed from the catheter porous section 12, for example, similar to the method of deploying the contrast fluid.

A distension device size can be determined as described, supra. The measurement tool 2 can be radially contracted and removed from the tunnel defect 84, or the coupler 72 and/or the elements of the measurement tool 2 proximal to the coupler 72 can be detached from the remainder of the measurement tool 2 and removed. If the entire measurement tool 2 is removed from the tunnel defect 84, a distension device can be selected that has a size that substantially matches (e.g., is equivalent when the distension device is in a substantially or completely radially expanded configuration) the size of the distended tunnel defect 84. The distension device can be deployed to the tunnel defect 84, for example along the guidewire 98. The guidewire 98 can be removed. The distension device can be, for example, a filter, stopper, plug, any distending device described in U.S. patent application Ser. Nos. 10/847,909, filed 19 May 2004; 11/184,069, filed 19 Jul. 2005; and 11/323,640, filed 3 Jan. 2006, all of which are incorporated by reference herein in their entireties, or any combinations thereof.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

We claim:

1. A device having a longitudinal axis, wherein the device is for measuring the width of a distended defect in tissue, the device comprising:
a first lateral elongated member, and wherein the first lateral elongated member is configured to expand away from the longitudinal axis, and wherein the first lateral elongated member is substantially parallel to the longitudinal axis, and wherein the first lateral elongated member has a first position near the longitudinal axis and a second position away from the longitudinal axis; and
a central elongated member, wherein the first lateral elongated member is attached to a first location of the central elongated member, and wherein the first lateral elongated member is received at a second location of the central elongated member, and wherein the first location is distal to the second location on the central elongated member.

2. The device of claim 1, further comprising a second elongated member, wherein the first elongated member is opposite with respect to the longitudinal axis to the second elongated member, and wherein the second elongated member is configured to expand away from the longitudinal axis.

3. The device of claim 2, further comprising a lumen.

4. The device of claim 3, further comprising a porous cover on the lumen.

5. The device of claim 2, wherein the central elongated member comprises a catheter, wherein the lumen is in the catheter.

6. The device of claim 5, wherein the catheter is fixedly attached to the first elongated member.

7. The device of claim 5, wherein the catheter is slidably attached to the first elongated member.

8. The device of claim 1, wherein the first elongated member is substantially flexible.

9. The device of claim 5, further comprising a coupler, wherein the coupler is attached to the catheter.

10. The device of claim 2, wherein the second elongated member is substantially flexible.

11. The device of claim 1, wherein the first elongated member comprises a wire body and a marker.

12. The device of claim 1, wherein the first lateral elongated member is coplanar with the longitudinal axis and the central elongated member.

13. The device of claim 1, wherein the first lateral elongated member is slidably received at the second location of the central elongated member.

14. A device having a longitudinal axis, wherein the device is for measuring the width of a distended defect in tissue, the device comprising:
a first lateral elongated member, and wherein the first lateral elongated member is configured to expand away from the longitudinal axis, and wherein the first lateral elongated member is substantially parallel with the longitudinal axis, and wherein the first lateral elongated member has a first position near the longitudinal axis and a second position away from the longitudinal axis; and
a central elongated member, wherein the first lateral elongated member is received at a first location of the central elongated member, and wherein the first elongated member is attached at a second location of the central elongated member, and wherein the first location is distal to the second location on the central elongated member.

15. The device of claim 14, wherein the first lateral elongated member is slidably received at the first location of the central elongated member.

16. The device of claim 14, further comprising a second lateral elongated member, wherein the first elongated member is substantially opposite with respect to the longitudinal axis to the second lateral elongated member, and wherein the second lateral elongated member is configured to expand away from the longitudinal axis.

17. The device of claim 14, wherein the central elongated member comprises a lumen and a porous length in fluid communication with the lumen.

18. The device of claim 14, wherein the first lateral elongated member is coplanar with the longitudinal axis and the central elongated member.

19. A device having a longitudinal axis, wherein the device is for measuring the width of a distended defect in tissue, the device comprising:
a first elongated member, and wherein the first elongated member is configured to expand away from the longitudinal axis, and wherein the elongated member is substantially parallel with the longitudinal axis, and wherein the elongated member has a first position near the longitudinal axis and a second position away from the longitudinal axis, and wherein the elongated member is a central elongated member, wherein the first elongated member is received at a first location of the central elongated member, and wherein the first elongated member is received at a second location of the central elongated member, and wherein the first location is distal to the second location on the central elongated member.

20. The device of claim 19, wherein the first lateral elongated member is slidably received at the first location of the central elongated member.

21. The device of claim 20, wherein the first lateral elongated member is slidably received at the second location of the central elongated member.

22. The device of claim 19, further comprising a second lateral elongated member, wherein the first elongated member is substantially opposite with respect to the longitudinal axis to the second lateral elongated member, and wherein the second lateral elongated member is configured to expand away from the longitudinal axis.

23. The device of claim 22, wherein the first elongated member is coplanar with the longitudinal axis and the second lateral elongated member.

* * * * *